United States Patent [19]

Musser et al.

[11] Patent Number: 4,778,931
[45] Date of Patent: * Oct. 18, 1988

[54] CERTAIN [3-(1-HYDROXY HEXYL-TETRAHYDRO)NAPHTHALENES], THE CORRESPONDING NAPHTHALENES HAVING ANTI-INFLAMMATORY AND ANTI-ALLERGIC ACTIVITY

[75] Inventors: John H. Musser, Malvern, Pa.; Utpal R. Chakraborty, Orangeburg, N.Y.

[73] Assignee: USV Pharmaceutical Corporation, Tuckahoe, N.Y.

[*] Notice: The portion of the term of this patent subsequent to Jan. 28, 2003 has been disclaimed.

[21] Appl. No.: 803,122

[22] Filed: Nov. 29, 1985

Related U.S. Application Data

[63] Continuation-in-part of Ser. No. 736,795, May 22, 1985, abandoned, which is a continuation-in-part of Ser. No. 530,811, Sep. 9, 1983, Pat. No. 4,567,184, which is a continuation-in-part of Ser. No. 445,876, Dec. 1, 1982, abandoned.

[51] Int. Cl.$^4$ .................. C07C 43/20; C07C 43/23; C07C 43/257; C07C 43/295
[52] U.S. Cl. .................. 568/633; 568/337; 568/638; 568/644; 568/645; 564/183; 560/61; 546/149; 546/152; 546/322; 546/326
[58] Field of Search .................. 568/633, 638

[56] References Cited

U.S. PATENT DOCUMENTS

| | | | |
|---|---|---|---|
| 2,862,956 | 12/1958 | Gundel et al. | 560/73 |
| 4,360,700 | 11/1982 | Melvin, Jr. | 568/644 |

FOREIGN PATENT DOCUMENTS

| | | | |
|---|---|---|---|
| 0113587 | 7/1984 | European Pat. Off. | 546/344 |
| 2253511 | 7/1975 | France | 568/331 |
| 175293 | 12/1976 | New Zealand | 568/644 |
| 184606 | 6/1979 | New Zealand | 560/61 |
| 202031 | 10/1984 | New Zealand | 546/153 |

OTHER PUBLICATIONS

Boots, et al., Journal of Pharmaceutical Sciences, vol. 62, No. 6, Jun. 1973.
European Search Report EP 83 11 2031.
Chemical Abstracts, vol. 94 (1981) 174, 888-b.

*Primary Examiner*—Alan L. Rotman
*Attorney, Agent, or Firm*—Scully, Scott, Murphy & Presser

[57] ABSTRACT

The invention relates to several aryloxy-alkane alcohols, for example 1-(3-(1-hydroxy-1-methylhexyl) phenoxy methyl)-2-methoxy-naphthalene, 2-(1-(3-(1-hydroxy-2,2-dimethylhexyl)phenoxy)ethyl naphthalene, 1-(3-6-phenoxy-1-hydroxyhexyl)phenoxy methyl)-4-methoxy naphthalene, 2-(3-(1-hydroxyhexyl) phenoxymethyl) naphthalene and 2-(3-(1-hydroxyhexyl)-phenoxymethyl)-1,2,3,4-tetrahydro naphthalene, methods for their preparation and their use for treating inflammatory and allergic conditions in a mammal.

5 Claims, No Drawings

CERTAIN [3-(1-HYDROXY HEXYL-TETRAHYDRO)NAPHTHALENES], THE CORRESPONDING NAPHTHALENES HAVING ANTI-INFLAMMATORY AND ANTI-ALLERGIC ACTIVITY

DESCRIPTION OF THE INVENTION

This application is a continuation-in-part of application Ser. No. 736,795, filed May 22, 1985 now abandoned which is a continuation-in-part of application Ser. No. 530,811, filed Sept. 9, 1983 now U.S. Pat. No. 4,567,184, which is a continuation-in-part of application Ser. No. 445,876, filed Dec. 1, 1982 now abandoned.

This invention relates to new chemical compounds possessing valuable pharmaceutical activity. More particularly, the invention relates to novel lipoxygenase inhibitor compounds possessing anti-inflammatory and anti-allergic activities.

The present new compounds are of the formula:

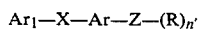

$$Ar_1-X-Ar-Z-(R)_{n'} \qquad I$$

and salts thereof, wherein $Ar_1$ is an aromatic hydrocarbon such as phenyl, naphthyl, phenanthryl or anthryl;

Ar is a phenyl group or a nitrogen, oxygen or sulfur heterocyclic group;

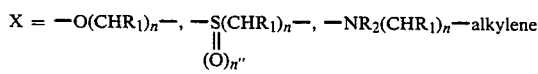

$$X = -O(CHR_1)_n-, \ -S(CHR_1)_n-, \ -NR_2(CHR_1)_n-\text{alkylene}$$
$$\underset{(O)_{n''}}{\|}$$

of up to 2 carbon atoms in the principal chain and up to a total of 4 carbon atoms,

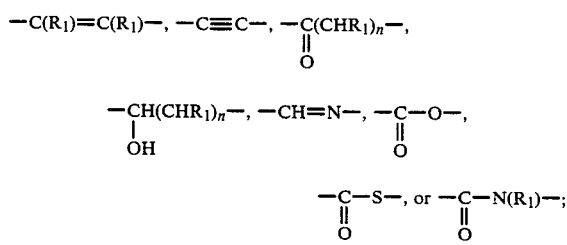

$$-C(R_1)=C(R_1)-, \ -C\equiv C-, \ -\underset{O}{\overset{\|}{C}}(CHR_1)_n-,$$

$$-\underset{OH}{\overset{|}{C}H}(CHR_1)_n-, \ -CH=N-, \ -\underset{O}{\overset{\|}{C}}-O-,$$

$$-\underset{O}{\overset{\|}{C}}-S-, \ \text{or} \ -\underset{O}{\overset{\|}{C}}-N(R_1)-;$$

Z is an alkylene chain containing up to 10 carbon atoms in the principal chain and a total of up to 12 carbon atoms and from 0 to 2 double bonds and the said alkylene chain may be attached to Ar through an oxygen, sulfur or amino nitrogen atom, and when $n'=2$, one of the R substituents may be halogen on an omega carbon of the alkylene chain Z;

when $n'=1$, R is a substituent attached to one of the carbon atoms of Z selected from the group consisting of =O, $OR_3$, $SR_3$, $N(R_2)_2$ and $-COR_4$, and when $n'$ 2 and R is as previously defined and the additional R is a substituent attached to one of the carbon atoms of Z selected from the group consisting of =O, $OR_3$, $SR_3$, $N(R_2)_2$, $-COR_4$ and halo;

$R_1$ is H or $CH_3$;

$R_2$ is H, lower alkyl, aryl or aralkyl;

$R_3$ is H, lower alkyl, lower alkanoyl, aryl, aralkyl or substituted aryl in which the substituent is halo, lower alkyl or lower alkoxy;

$R_4$ is $OR_2$ or $N(R_2)_2$;

$n=0$ or 1;

$n'=1$ to 4; and $n''=0$, 1 or 2.

In the foregoing description, the lower alkyl and alkanoyl groups contain up to 6 carbon atoms which may be in the normal or branched configuration, including methyl, ethyl, propyl, isopropyl, butyl, isobutyl, amyl, isoamyl, hexyl, and the like. The aryl group is preferably phenyl, and aralkyl is benzyl. The alkanoyl group is preferably acetyl.

Ar is preferably a monocyclic ring, e.g. phenyl, pyridine, thiophene, furan and pyrrole, and especially phenyl while $Ar_1$ is preferably a monocyclic or bicyclic ring e.g., phenyl or naphthyl. These rings are attached in their respective positions in the molecule of the present new compounds through any available carbon of the ring, but preferably through the 2-position of $Ar_1$.

Ar and $Ar_1$ may be fully substituted or less than fully substituted, e.g., mono- or di- or tri- or tetra-substituted with a variety of substituents such as H, $CH_3$, lower alkyl, aryl, aralkyl, halo, hydroxy, lower alkoxy, $CF_3$, carboxy, alkylcarboxy, arylcarboxy, alkylcarbalkoxy, alkanoyl, formyl, oxo, nitrilo, amino, aminoalkyl, alkylamine, carboxamide, aryloxy, nitro, sulfonyl, sulfonamide, thio, alkylthio, hydroxyalkyl or oxyalkylcarbalkoxy.

It is preferred that the same substituents be present in intermediate compounds used in forming the final products as described in the disclosure of methods of preparation which follows. The substituents may be present on any of the available positions of the ring systems representative or Ar and $Ar_1$. Of course, substituents which are reactive under the synthetic conditions employed should be blocked using appropriate blocking groups which are readily removable after formation of the desired products. Such blocking groups are well known to those skilled in this art.

The alkylene chains represented by Z can be normal or branched chains in which the branches are preferably methyl or ethyl and include those in which two such groups, e.g., methyl, are on the same carbon atom. The alkylene chains preferably contain up to 8 carbon atoms whether branched or normal. The alkylene chain may contain up to 2 double bonds and may be attached directly to the Ar ring through an oxygen, sulfur or amino nitrogen atom. In addition to substituent R, which is attached to one of the carbon atoms as depicted in the foregoing formula, other substituents such as halogen (F, Cl, Br or I) can be present on the alkylene chain, particularly on the terminal carbon.

Of the various groups representative of X in the foregoing formula, the preferred are those in which $n=1$, and especially those which include an oxygen function, particularly the group $-O(CHR_1)_n-$ in which n is 1 and $R_1$ is H. The disposition of the said groups between Ar and $Ar_1$ is not critical, e.g., the $-O(CHR_1)_n-$, can be attached with the oxygen directly on $Ar_1$ or on Ar. Preferably, the oxygen of $-O(CHR_1)$ is attached to $Ar_1$.

In the most preferred compounds of this invention, Ar is phenyl, $Ar_1$ is phenyl or naphthyl, X is $-OCH_2-$, Z is alkylene of from about 5–8 carbon atoms and R is oxygen-containing group, preferably, hydroxy, and $n'$ is 1.

The present new compounds can be prepared by art-recognized procedures. For compounds in which $X=-O(CHR_1)_n$, any of the standard ether forming reactions can be employed as illustrated by the following general procedures:

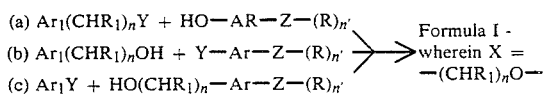

(a) $Ar_1(CHR_1)_nY + HO-Ar-Z-(R)_{n'}$
(b) $Ar_1(CHR_1)_nOH + Y-Ar-Z-(R)_{n'}$
(c) $Ar_1Y + HO(CHR_1)_n-Ar-Z-(R)_{n'}$

Formula I - wherein $X = -(CHR_1)_nO-$

In these modifications, Y is a leaving group, most commonly halogen, preferably Cl, Br or I, which forms HY with the hydrogen of the alcohol. Illustrative of processes (a) and (b), chloromethylbenzene is condensed with 1-(3-hydroxyphenyl)-1-pentanol and hydroxymethylbenzene is condensed with 1-(3-bromophenyl)-1-pentanol to form the same product. Illustrative of process (c) is the condensation of bromobenzene with 5-(1-hydroxyhexyl)furfuryl alcohol to form the corresponding phenyl-furylmethyl ether. Alternatively, the leaving group can be a sulfonate ester group, such as the tolyl sulfonate group, which forms toluenesulfonic acid with the hydrogen of the OH group. In all cases where an acid is the by-product, it is preferred to use an acid acceptor to neutralize the acid in the reaction mixture. Such acid acceptors are well-known in the art and include various alkali and alkaline earth metal carbonates and bicarbonates, e.g., sodium carbonate, potassium bicarbonate, cesium carbonate and the like, alkali metal alkoxides such as sodium ethoxide, potassium ethoxide and the like, as well as organic amines such as pyridine, pyrrole, dimethylamine, and similar such amines. Of course, when $Ar_1$ and/or Ar includes a basic nitrogen heteroatom, this can serve as the acid acceptor and the product is obtained as an acid salt.

To form compounds in which X is

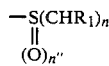

$$-\underset{\underset{(O)_{n''}}{\|}}{S}(CHR_1)_n$$

the same reactions can be used employing the corresponding mercaptans in lieu of the alcohols. The sulfoxides and sulfones (where $n'' = 1$ or 2) can be formed by the known reaction with peroxides such as hydrogen peroxide or benzoylperoxides.

For compounds in which X is $-NR_2-(CHR_1)_n-$, the corresponding amino starting compounds are employed to form the desired amino compound. Thus, aniline is condensed with 3-(1-hydroxyhexyl)benzylbromide to form 2-[3-(1-hydroxyhexyl)benzylamino]benzene. Alternatively, benzyl bromide is condensed with 3-(1-hydroxyhexyl)aniline to form 2-[3-(1-hydroxyhexyl)anilinomethyl]benzene.

Compounds in which X is $-CH=N$ are so-called anils and are prepared by condensing an aldehyde with the corresponding amine. Thus, aniline can be condensed with 5-(1-hydroxybutyl)furfural to form the corresponding anil. Alternatively, thiophene-2-aldehyde can be condensed with 5-(1-hydroxypentyl)benzylamine to from the corresponding anil.

For those compounds in which X is

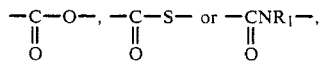

$$-\underset{\underset{O}{\|}}{C}-O-, \quad -\underset{\underset{O}{\|}}{C}-S- \quad \text{or} \quad -\underset{\underset{O}{\|}}{C}NR_1-,$$

the acid $Ar_1COOH$ is esterified with $HO-Ar-Z-(R)_{n'}$, or the corresponding mercaptans, and the amide is formed by reaction of a suitable derivative of the acid and the amine, $HNR_1Ar-Z-(R)_{n'}$. Since the group $-Z(R)_{n'}$ may contain a group reactive with the aforesaid acid derivatives, it is preferred that the desired group $-Z(R)_{n'}$ be formed after the acylation reaction is completed. This can be accomplished by providing a group convertible to the desired group in the Ar nucleus. Such convertible groups include, for example, the nitrilo and formyl groups, which after acylation, can be converted to aminoalkyl in the case of the nitrilo group or to hydroxyalkyl in the case of the formyl group, e.g., by reaction with a Grignard reagent to form a secondary alcohol of any desired carbon length. The position of the amino or alcohol hydroxy groups can be set by merely selecting the length of carbon chain (where present) separating the nitrilo or formyl group from the Ar ring carbon as should be obvious to those skilled in the art.

Of course, the group $-Z(R)_{n'}$ may contain groups which are non-reactive in formation of the X linkage between Ar and $Ar_1$ and such groups as are non-reactive may be present in the Ar nucleus before such formation, e.g., ether groups such as alkoxy, alkylmercapto, phenoxy, and the like, keto-carbonyl, alkoxy-carbonyl and carboxamido groups. After formation of the X-linkage, such non-reactive groups can be converted to 1°, 2° or 3+ alcohol groups by reduction of a carbonyl or reaction with a Grignard reagent with the carbonyl or by reduction of an ester group, $COOR_4$.

For compounds in which Z is ethylenic, $Ar_1CH_2Y$ is condensed with

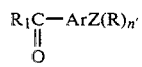

$$R_1\underset{\underset{O}{\|}}{C}-ArZ(R)_{n'}$$

to form the desired ethylenic compound. From those in which $R_1$ is H, the corresponding acetylenic compounds can be obtained by halogenation to form the dihalo compound and dehydrohalogenation to remove 2 equivalents of hydrogen halide.

Many obvious variations of the foregoing procedures will be apparent to those skilled in the art for preparing compounds of the invention.

The compounds of the invention containing basic nitrogen form salts with acids, both organic and inorganic acids. Of particular value are salts with pharmaceutically-acceptable acids especially in dosage forms predicated on aqueous systems where the enhanced water solubility of the salts is most advantageous. Salts formed with pharmaceutically unacceptable acids are also useful in the isolation and purification of the basic nitrogen-containing present new compounds. Salts include those formed with hydrochloric, sulfuric, nitric, perchloric, benzenesulfonic, toluenesulfonic, phosphoric, acetic, malic, malonic, tartaric and similar such acids.

The compounds of the invention also exist in stereoisomeric forms due to the presence of asymmetric centers in the molecule, especially in the group $-Z(R)_{n'}$ and in the linkage $-X-$ (where $R_1$ is other than H) or in other parts of the molecule. This invention contemplates the stereoisomers individually or in mixtures or as the racemic compound. The individual stereoisomers can be obtained by standard resolution procedures known to those skilled in the art or by stereospecific synthesis.

The compounds of the present invention can be administered to the host in a variety of forms adapted to the chosen route of administration, i.e., orally, or parenterally. Parenteral administration in this respect includes administration by the following routes: intravenous, intramuscular, subcutaneous, intraocular, intrasynovial, transepithelially including transdermal, ophtalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, or course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for exmple, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosage by small increments until the optimum effect under the circumstances is reached. The therapeutic dosage will generally be from 0.1 to 100 $\mu$M/day or from about 0.1 mg to about 50 mg/kg of body weight per day and higher although it may be administered in several different dosage units. Higher dosages are required for oral administration.

The following examples are illustrative.

EXAMPLE 1A

Methyl-2-bromomethylbenzoate

A water jacketted, immersion photolysis vessel equipped with a $N_2$ inlet, dropping funnel and a reflux condenser was charged with 1 L of carbon tetrachloride and 127 g. (0.847 mol) of 2-methyl toluate (Pfaltz and Bauer M29200). A solution of 400 ml carbon tetrachloride and 43.5 ml (0.849 mol) of bromine was added to the dropping funnel. After the solution had been heated to reflux the bromine solution was slowly added while the solution was irradiated with a 600 watt incandescent lamp. After the addition of the bromine solution was complete, the lamp was turned off and the solution cooled. The carbon tetrachloride was removed under reduced pressure. The resultant oil was crystallized from 250 ml of a (1:1) solution of diethyl ether and hexane. The solid was collected and washed with hexane to yield 119 g. (61%) of product.

In like manner, as above, using appropriate starting materials, the following compounds were prepared:
  Methyl-3-bromomethylbenzoate;
  Methyl-4-bromomethylbenzoate; and
  Methyl-3-bromomethylphenylacetate.

EXAMPLE 1B 1-(3-Hydroxyphenyl)-1-pentanol

A dried 1 L 3-neck flask equipped with a $N_2$ inlet, reflux condenser, mechanical stirrer and a 500 ml dropping funnel was charged with 24.3 g (1.0 mol) of magnesium and 50 ml of anhydrous ether. To this was added 15 g. (0.11 mol) of 1-bromobutane (Aldrich 23,988-7) and one crystal of iodine. The dropping funnel was charged with 122 g. (0.89 mol) of 1-bromobutane and 100 ml of anhydrous ether. After the contents of the reaction flask began to reflux, the flask was cooled with a water/ice bath and the 1-bromobutane solution was added at such a rate as to maintain a gentle reflux. After the addition was complete the reaction mixture was refluxed for one-half hour, then cooled to 0° C. in an ice/water bath. The dropping funnel was then charged with 38.0 g (0.311 mol) of 3-hydroxybenzaldehyde (Aldrich H 1,980-8) and 250 ml of anhydrous ether. This slurry was added over a 1 hour period. After the addition the reaction mixture was allowed to warm up to room temperature and was stirred overnight. The reaction mixture was neutralized with 900 ml of 5% aqueous HCl. The reaction mixture was extracted with $2\times500$ ml of ethyl acetate, the organic extracts combined, washed with 1 L of water, dried over anhydrous sodium sulfate and concentrated under reduced pressure. The crude product was recrystallized from ethyl acetate to yield 44.0 g. (79%) of 1-(3-hydroxyphenyl)-1-pentanol, m.p. 120°-122° C.

In like manner as above, using appropriate starting materials and reagents, the following compounds were prepared:
  1-(3-Hydroxyphenyl)-1-hexanol;
  1-(2-Hydroxyphenyl)-1-hexanol;
  2-(3-Hydroxyphenyl)-2-heptene;
  1-(4-Hydroxyphenyl)-1-hexene;
  Phenyl-3-[1-(hydroxy)hexyl]benzyl ether; and
  1-(3-Phenoxyphenyl)-1-hexanol.

EXAMPLE 1C

Methyl-2-[[3-(1-hydroxypentyl)phenoxy]methyl]benzoate

To a 1 L 3-neck round bottom flask was added 45.2 g. (0.197 mol) of methyl O-bromomethylbenzoate, 35.5 g (0.197 mol) of 1-(3-hydroxyphenyl)-1-pentanol, 3.0 g (0.020 mol) of sodium iodide, 64.3 g. (0.198 mol) of cesium carbonate and 500 ml of acetone. This slurry was refluxed for 3½ days. At which time the reaction mixture was cooled, solid removed by suction filtration and the solvent removed under reduced pressure. The resulting oil was partitioned between 10% aqueous HCl and ethyl acetate. The organic extract was washed with 200 ml of water, dried over anhydrous sodium sulfate and concentrated to yield 65.2 g of oil. A silica gel chromatography using hexane/chloroform (1:2) as eluent afforded 54.7 g. (85%) of product as an oil. In like manner as above, using appropriate starting materials and reagents, the following compounds were prepared:

Methyl-3-[[3-(1-hydroxyhexyl)phenoxy]methyl]benzoate;
  Methyl-2-[[3-(1-hydroxyhexyl)phenoxy]methyl]benzoate;
  Methyl-4-[[3-(1-hydroxyhexyl)phenoxy]methyl]benzoate;
  Methyl-3-[[2-(1-hydroxyhexyl)phenoxy]methyl]benzoate;
  Methyl-3-[[3-(1-hydroxyhexyl)phenoxy]methyl]phenylacetate;
  3-[[3-(1-Hydroxyhexyl)phenoxy]methyl]benzonitrile;
  Methyl-2-[4-[[3-1-hydroxyhexyl)phenoxy]methyl]phenoxy]acetate;
  Benzyl-3-[1-(hydroxy)hexyl]phenyl ether;
  Methyl-3-[[3-1-methyl-1-hexenyl)phenoxy]methyl benzoate;
  Methyl-3-[[4-(1-hexenyl)phenoxy]methyl benzoate;
  Phenyl-3-cyanobenzyl ether;
  3-(1-Hydroxyhexyl)phenyl-3-trifluoromethylbenzyl ether;
  2-[(3-(1-Hydroxyhexyl)phenoxy methyl naphthalene]

EXAMPLE 2

2-[[3-(1-Hydroxyhexyl)phenoxy]methyl]benzoic acid

A solution of methyl-2-[[3-(1-hydroxyhexyl)phenoxy]methyl]benzoate (1.0 g.) in 50 ml of methanol was treated with 1N aqueous sodium hydroxide. The reaction was stirred for 1 hour at room temperature. The mixture was washed with ethyl ether, acidified with 5% aqueous hydrochloric acid and extracted with chloroform. The chloroform extract was dried ($MgSO_4$) and concentrated to a solid (0.7 g., 73% yield), m.p. 76°-80° C.

In like manner as above, using appropriate starting materials, the following compounds were prepared:
  3-[[3-1-Hydroxyhexyl)phenoxy]methyl]benzoic acid;
  2-[[3-1-Hydroxyhexyl)phenoxy]methyl]benzoic acid, m.p. 115°-115.5° C.;
  4-[[3-(1-Hydroxyhexyl)phenoxy]methyl]benzoic acid, m.p. 105°-6° C.;
  3-[[3-(1-Hydroxyhexyl)phenoxy]methyl]phenyl acetic acid; and

EXAMPLE 3

Methyl-3-[[3-(1-acetoxyhexyl)phenoxy]methyl]benzoate

To a solution of methyl-3-[[3-(1-hydroxyhexyl)phenoxy]methyl]benzoate (1.7 g.) in pyridine at 0° C. was added acetic anhydride (2.7 ml). The reaction was stirred for four days at room temperature. The solvent was removed in vacuo and the remaining oil was purified by HPLC on silica gel using a hexanes/ethyl acetate in 9:1 ratio as an eluent (1.1 g., 57% yield).

EXAMPLE 4

Methyl-3-[[3-(1-methoxyhexyl)phenoxy]methyl]benzoate

To a suspension of sodium hydride (0.5 g.) in ethyl ether at 0° C. was added methyl-3-[[3-(1-hydroxyhexyl)phenoxy]methyl]benzoate (1.7 g.) in ether. The mixture was allowed to warm to room temperature. Methyl iodide (0.6 ml) was added and the reaction was stirred at room temperature for three days. The reaction was quenched with saturated aqueous ammonium chloride. Th mixture was extracted with ethyl ether. The organic extract was washed with water, dried ($MgSO_4$) and concentrated to an oil. The oil was purified by HPLC on silica gel using a 1:9 ratio of ethyl acetate/hexanes as an eluent.

EXAMPLE 5

Methyl-3-[[3-[1-(tetrahydro-2H-pyran-2-yloxy)hexyl]-phenoxy]methyl]benzoate

To a solution of methyl-3-[[3-(1-hydroxyhexyl)-phenoxy]methyl]benzoate (2.2 g), dihydropyran (2.3 ml) and ethyl ether was added a catalytic amount of para-toluene sulfonic acid. The reaction was stirred at room temperature for four days. The ethyl ether was removed in vacuo and the remaining oil was purified by HPLC on silica gel using 7:93 ratio of ethyl acetate/hexanes as an eluent (1.8 g., 67% yield). In like manner as above, using appropriate starting materials, the following compound was made:

Methyl-2-[[3-[1-(tetrahydro-2H-pyran-2-yloxy)pentyl]phenoxy]methyl]benzoate.

EXAMPLE 6

2-[3-(1-Hydroxypentyl)phenoxy]methyl]benzenemethanol

To a suspension of lithium aluminum hydride (1.0 g.) in ethyl ether (100 ml) at 0° C. was added dropwise a solution of methyl-4-[[3-(1-hydroxyhexyl)phenoxy]methyl]benzoate (3.2 g.) in ethyl ether (100 ml). The reaction was consecutively quenched with 1 ml of water, 1 ml of 15% sodium hydroxide and 3 ml of water. The mixture was filtered and the ethyl ether was removed in vacuo (1.9 g., 65% yield).

EXAMPLE 7

3-[[3-(1-Hydroxyhexyl)phenoxy]methyl]benzaldehyde

To a solution of 3-[[3-(1-hydroxyhexyl)phenoxy]methyl]benzonitrile (10.0 g). in THF was added diisobutylaluminum hydride (15 g.) and the reaction was refluxed overnight. Methanol (10.2 ml) was slowly added followed by water (5.7 ml). The mixture was filtered and the filtrate was concentrated to an oil. The oil was dissolved in chloroform. The solution was washed with 5% aqueous hydrochloride acid (4 times), dried (MgSO4) and concentrated to an oil (3.0 g., 30% yield). In like manner as above, using appropriate starting materials, the following intermediate was prepared:

Phenyl-3-formylbenzyl ether.

EXAMPLE 8

3-[[3-(1-Hydroxyhexyl)phenoxy]methyl]benzyl amine hydrochloride

To a suspension of lithium aluminum hydride (1.0 g.) in ethyl ether, was added dropwise a solution of 3-[[3-(1-hydroxyhexyl)phenoxy]methyl]benzonitrile (3.0 g.) in ethyl ether. After stirring for 2 hours at room temperature the reaction was quenched consecutively with 1 ml H2O, 1 ml 15% sodium hydroxide and 3 ml of water. The mixture was filtered. The remaining solution was treated with ethereal hydrochloric acid and a precipitate formed. The precipitate was filtered and dried, giving 2.2 g (63% yield) of solid, m.p. 90°-94° C.

EXAMPLE 9

3-[[3-(1-hydroxyhexyl)phenoxy]methyl]benzamide

A mixture of 3[[3-(1-hydroxyhexyl)phenoxy]methyl]benzonitrile (5.0 g.), 30% hydrogen peroxide (6.6 ml), ethanol (9 ml) and 6N sodium hydroxide (0.7 ml) was stirred at room temperature for one hour. The reaction was then heated to 50° C. for three hours. The solution was neutralized with 5% aqueous hydrochloric acid and extracted with chloroform. The organic extract was dried (MgSO4) and concentrated to a solid. The solid was recrystallized from ethyl acetate giving 3.4 g (63%) yield) of solid, m.p. 97°-98° C.

In like manner as above, using appropriate starting materials, the following compound was prepared: 3-[3-hexanoyl phenoxy]methyl benzamide.

EXAMPLE 10

Benzyl-3-(hexanoyl)phenyl ether

To a suspension of pyridinium chlorochromate (32.3 g) in methylene chloride (200 ml) was added a solution of benzyl-3-[1-hydroxyhexyl]phenyl ether (28.4 g.) in methylene chloride (25 ml). The reaction was stirred at room temperature for 1½ hours. The excess methylene chloride was decanted and residual black solid was triturated with ethyl ether (four times.) The combined organic extract was purified on flurosil using ethyl ether as an eluent (27.5 g., 98% yield).

In like manner as above, using appropriate starting materials and reagents, the following compound was prepared:

3-[3-Hexanoyl phenoxy]methyl benzonitrile.

EXAMPLE 11

Benzyl-3-[1-(N-methylamino)hexyl]phenyl ether

A solution of benzyl-3-(hexanoyl)phenyl ether (2.8 g.), 40% aqueous methylamine (1.5 ml) and methanol adjusted to pH 6 with 5% aqueous hydrochloric acid is treated with a methanolic solution of sodium cyanoborohydride. The reaction is stirred overnight. The methanol is removed in vacuo and the remaining mixture is extracted with methylene chloride. The organic extract is dried (MgSO4) and concentrated to an oil.

In like manner as above, using appropriate starting materials, the following compounds can be prepared:

3-Chlorobenzyl-3-[1-(n-butylamino)hexyl]phenyl ether; and

2-Trifluoromethyl-3-[1-(N,N-dimethylamino)hexyl]phenyl ether.

EXAMPLE 12

Benzyl-3-[1-hydroxy-2,2-(dimethyl)hexyl]phenyl ether

To a solution of lithium amide (0.36 g.) and methyl iodide (3.02 g.) in THF (10 ml) at reflux is slowly added a solution of benzyl-3-(hexanoyl)phenyl ether (2.0 g) in THF (10 ml). The reaction is heated at reflux for two hours. The THF is removed in vacuo. The residue is dissolved in ethyl acetate, washed with water and brine; dried (MgSO4) and concentrated to an oil. The oil is dissolved in ether and slowly added to a suspension of lithium aluminum hydride (0.1 g.) in ethyl ether. The reaction is then heated at reflux for two hours. The reaction is quenched by consecutive treatment with water (0.1 ml), 1N NaOH (0.3 ml), water (0.1 ml). The mixture is filtered and the ethyl ether is removed in vacuo giving the desired oil.

In like manner as above, using appropriate starting materials and reagents, the following compounds can be prepared:

2,4-Dibromobenzyl-3-[1-(hydroxy)2-(isobutyl)hexyl]phenyl ether; and

4-Fluorobenzyl-3-[1-(hydroxy)2-(diethyl)heptyl]phenyl ether; and

Benzyl 3-(1-hydroxy-2-methyl hexyl)phenyl ether.

EXAMPLE 13

3-(1-Hydroxyhexyl)benzyl alcohol

To a solution of pentyl magnesium bromie (0.082 mol) in ethyl ether (100 ml) at 0° C. as prepared in Example 2 is added cadmium chloride (8.06 g) portionwise. The suspension is stirred overnight at room temperature. The solvent is distilled and toluene (300 ml) is added. The mixture is refluxed for one hour and cooled to room temperature. A solution of 3-carbomethoxy benzoyl chloride (48 g.) in toluene (50 ml) is slowly added. The reaction is refluxed for two hours. After cooling, 3% aqueous hydrochloric acid is added. The organic phase is separated and the aqueous phase is extracted with ethyl acetate. The combined extracts are dried (MgSO$_4$) and concentrated to an oil. The oil is dissolved in ethyl ether and slowly added to a suspension of lithium aluminum hydride (4.0 g.) in ethyl ether. The reaction is heated at reflux for two hours. The reaction was quenched by consecutive treatment with water (4 ml), 1N NaOH (12 ml) and water (4 ml). The mixture is filtered and the ethyl ether is removed in vacuo giving the desired oil.

EXAMPLE 14

Tolyl-3-(1-hydroxyhexyl)benzyl sulfonate

To a solution of 3-(1-hydroxyhexyl)benzyl alcohol (20.8 g.) in pyridine (50 ml) is added para-toluenesulfonyl chloride (20.1 g.). The reaction is stirred at room temperature for two days. Ice is added and the mixture is extracted with ethyl ether (twice). The organic extract is washed with 5% aqueous hydrochloric acid (four times), brine; dried (MgSO$_4$) and concentrated to an oil.

EXAMPLE 15

Methyl-3-[[3-(1-hydroxyhexyl)anilinyl]methyl]benzoate

A mixture of tolyl-3-(1-hydroxyhexyl)benzyl sulfonate (3.6 g.), methyl-3-aminobenzoate (1.5 g.) (Pfaltz and Bauer M10720), cesium carbonate (3.2 g.) and toluene (200 ml) is refluxed for two days. The reaction is filtered and concentrated to an oil. The oil is purified by HPLC on silica gel. In like manner as above, using appropriate starting materials and reagents, the following compounds can be prepared:

Ethyl-2-[[3-(1-hydroxybutyl)anilinyl]methyl]benzoate;

Isopropyl-4-[[3-(1-hydroxybutyl)anilinyl]methyl]benzoate;

Methyl-3-[[2-(1-hydroxyhexyl)anilinyl]methyl]benzoate;

Phenyl-3-[1-(hydroxy)hexyl]benzyl thioether;

3-Methoxyphenyl-3-[1-(hydroxy)hexyl]benzyl thioether;

4-Nitrophenyl-3-[1-(hydroxy)hexyl]benzyl thioether; and

Methyl-2-[[3-(1-hydroxyhexyl)thiophenoxy]methyl]benzoate.

EXAMPLE 16

Methyl 3-[3-(1-hydroxyhexyl)phenyl)amino]carbonyl]benzoate

Dimethyl isophthalate (100 g) was mixed with potassium hydroxide (30 g) in methanol (700 ml) and water (500 ml), and refluxed for two hours. The reaction mixture was extracted thoroughly with ether to remove any unreacted diester present, and then the aqueous solution was acidified with cold, dilute HCl (6N). The white precipitate was filtered, dried and treated with ether-methanol. The insoluble diacid was filtered off, and the pure desired mono-ester was crystallized from the ether-methanol solution as a while solid (59 g).

A solution of methyl 3-carboxybenzoate (9 g), as prepared above, in methylene chloride (150 ml)-tetrahydrofuran (25 ml) solution was treated with oxalyl chlorie (9.5 g), and dimethyl formamide (4 drops). The mixture was stirred at room temperature for one hour, and then all volatiles were removed by reduced pressure distillation. The acid-chloride of methyl 3-carboxybenzoate was otained as a pale yellow liquid.

To a solution of the above acid chloride (9.9 g) in methylene chloride (75 ml) was added a mixture of triethylamine (6.3 g) and 3-aminobenzaldehyde diethylacetal (9.75 g); 3-aminobenzaldehyde diethylacetal was prepared by reducing (H$_2$, Pd-C, MeOH) 3-nitrobenzaldehyde diethyl acetal, which in turn was made by acetalization of 3-nitrobenzaldehyde with triethylorthoformate and p-toluenesulfonic acid in ethanol). The mixture of the acid chloride and the primary amine was stirred at room temperature overnight, and poured carefully into cold water. The organic layer was separated, dried over anhydrous magnesium sulfate, and then all solvent was removed. The residue was dissolved in tetrahydrofuran, and then dilute HCl solution (1N) was added till the mixture remained homogeneous. This mixture was stirred at room temperature for one hour, and then most of the volatile solvent was removed. The aqueous solution was extracted with ethyl acetate, and the organic extract was washed with water, saturated sodium bicarbonate, and finally brine. All volatiles were removed, and the residual solid was crystallized from methanol-hexanes to give pure methyl 3-(3-formyl)phenylaminocarbonyl benzoate as a white solid.

The above aldehyde (1.5 g) was dissolved in dry tetrahydrofuran, and cooled in an ice bath. To this cold solution was added dropwise, a solution of pentylmagnesiumbromide (prepared from 1-bromopentane (1.9 g) and magnesium turnings (0.31 g) in dry ether). The reaction mixture was stirred at 0° C. for two hours, and allowed to warm up to room temperature. The reaction mixture was carefully poured into cold water, and then extracted with ethyl acetate. The organic extract was washed with dilute HCl solution (0.1N), brine and then dried over anhydrous magnesium sulfate. All volatiles were removed to leave a viscous liquid (2 g) which quickly solidified on standing. This solid was crystallized from ethyl acetate-hexanes to give the pure desired material. In like manner, using appropriate starting materials and reagents, the following compound was prepared: 2-(3-(1-Hydroxyhexyl)phenylaminocarbonyl)benzoic acid, m.p. 114°–117° C.

EXAMPLE 17

Methyl 3-[3-[1-hydroxy-2,2-dimethylhexyl]phenoxy]methyl]-benzoate

A mixture of 3-(1-hydroxy-2,2-dimethylhexyl)phenol (0.7 g); prepared by the hydrogenolysis ($H_2$, 10% Pd-C, MeOH) of benzyl 3-(1-hydroxy-2,2-dimethylhexyl)phenyl ether made in Example 14), methyl 3-bromomethyl benzoate (0.72 g), potassium carbonate (0.45 g) and sodiuim iodide (0.05 g) in acetone (25 ml) was refluxed overnight. The reaction mixture was cooled, and poured into water. The aqueous solution was extracted with ethyl acetate. The organic extract was dried over magnesium sulfate, and then all volatiles were removed. The residual liquid (1.2 g) was purified by chromatography (silica gel; 18% ethyl acetate in hexanes) to isolate the desired ester as a clear, colorless liquid.

EXAMPLE 18

2-(3-Hexanoylphenoxy)methyl naphthalene

A solution of 1-(3-hydroxyphenyl)-1-hexanol (3 g) (made in Example 1B) in methylene chloride (200 ml) was added to a well-stirred suspension of pyridinium chlorochromate (5.1 g) and sodium acetate (2.5 g) in methylene-chloride (150 ml). The mixture was stirred at room temperature for two hours. Ether (100 ml) was added, and the brown granular precipitate was removed by filtration. All volatiles were removed from the filtrate, and the residual liquid was purified by chromatography on silica gel using ether as eluent. The desired ketone, 3-hexanoylphenol, was isolated as a clear, colorless oil.

This ketone (1.2 g) was refluxed with chloromethylnaphthalene (1.3 g), potassium carbonate (8.6 g), postassium iodide (0.05 g) and cesium carbonate (0.05 g) in acetone (300 ml) for 24 hours. The reaction mixture was filtered, and the filtrate was concentrated, dissolved in chloroform, and then washed with sodium hydroxide solution (5%), water and brine. After drying, all volatiles were removed. The residue was purified by chromatography on silica gel (25% ethyl acetate in hexanes). The pure desired product was isolated as a tan solid, m.p. 52°–55° C.

EXAMPLE 19

2-(3-Benzyloxyphenyl)-2-heptanol

To an ethereal solution of benzyl 3-hexanoylphenyl ether (3 g) made in Example 10 was added slowly an excess of methylmagnesium bromide (2.5 g; 7.0 ml of a 3M solution in ether). The reaction mixture was stirred overnight. A saturated solution of ammonium chloride was added dropwise to the well-stirred reaction mixture until the solution became clear, and a gray-white solid coagulated to form a hard cake. The liquid was filtered, and the residue was washed with more ether. The ether layer was separated from the aqueous layer, washed with brine, and dried over magnesium sulfate. All volatiles were removed to give an oil, which was purified by chromatography on silica gel (6% ethyl acetate in hexanes) to get the desired tertiary alcohol as a clear, colorless liquid.

In like manner as above, using appropriate starting materials and reagents, the following compounds were prepared:

2-(3-Benzyloxyphenyl)-3,3-dimethyl-2-heptanol; and 2-(3-(2-(2-Hydroxyheptyl)phenoxy)methyl naphthalene.

EXAMPLE 20

Trans-3-hexanoyl stilbene

A mixture of α-bromo-m-tolunitrile (20 g) and triethylphosphite (29.1 g) was heated gently in a round-bottomed flask fitted with a distilling head. Ethyl bromide that formed was removed by distillation. When no more ethyl bromide was distilling, the residual liquid was distilled under reduced pressure to isolate the phosphonate as a clear, colorless liquid: 22 g, bp. 152°–154° C./0.02 mm.

The phosphonate (22 g) was dissolved in dry tetrahydrofuran, and added dropwise to a well-stirred suspension of sodium hydride (4.2 g; 50% oil suspension) in dry tetrahydrofuran. After the addition was complete, the mixture was stirred at room temperature for one hour, cooled in an ice bath, and then a solution of benzaldehyde (9.2 g) in dry tetrahydrofuran was added slowly. The mixture was allowed to warm up, and stirred at room temperature overnight. The excess of sodium hydride was destroyed by adding cold methanol, and then all volatiles were removed. The residue was taken up in ethyl acetate, and washed with HCl solution (5%), water and brine. The organic extract was dried and then all volatiles were removed. The crude product (18 g), trans-3-cyano stilbene, was isolated as a light orange solid, m.p. 69°–71° C.

To a solution of n-pentylmagnesium bromide (prepared from 1-bromopentane (7.3 g) and magnesium turnings (1.2 g) in tetrahydrofuran) was added a solution of the above cyano compound (9 g) in tetrahydrofuran, all at once. The resulting deep-red solution was refluxed for 8 hours. A solution of hydrochloric acid (6N) was added (24 ml) to the cold (0° C. ) reaction mixture, and again refluxed for 8 hours. The mixture was cooled, and most tetrahydrofuran was removed at the rotary evaporator. The residue was dissolved in ethyl acetate, and the organic extract was washed with saturated sodium bicarbonate solution, brine, and then dried over magnesium sulfate. The solvent was removed to yield the crude material (15 g), which was purified by chromatography (silica gel; 3% ethyl acetate in hexanes). The desired trans-stilbene ketone was isolated as a white solid, m.p. 54°–56° C.

EXAMPLE 21

Trans-3-(1'hydroxyhexyl) Stilbene

The ketone, trans-3-hexanoyl stilbene of Example 20 (1 g) was dissolved in ethanol, and sodium borohydride (0.2 g) was added. The mixture was stirred overnight. Excess of the borohydride was destroyed by carefully adding a dilute HCl solution. The aqueous solution was extracted thoroughly with ether, and then the ether extract was washed with brine and dried. On removal of all volatiles, the pure alcohol was obtained as a clear, colorless liquid in quantitative yield.

In like manner as described above, using appropriate starting materials and reagents, the following compounds were prepared:

cis-3-(1-Hydroxyhexyl)stilbene;
1-(3-(2-Phenylethyl)phenyl-1-hexanol; and
3-(1-Hydroxyhexyl)diphenylacetylene.

EXAMPLE 22 cis-3-Hexanoyl Stilbene

To a solution of triphenylphosphine (29.5 g) in toluene (150 ml) was added a solution of α-bromo-m-tolunitrile (20 g) in toluene (50 ml), and the mixture was stirred at room temperature for one day. The white precipitate was filtered off and washed with toluene and ether to get the phosphonium bromide as a white solid.

The phosphonium salt (15 g) was dissolved in dry dimethylsulfoxide (100 ml), cooled to 0° C., and then a solution of n-butyl lithium in hexane (49.3 mmol) was added dropwise. The mixture became red and cloudy. It was allowed to warm up to room temperature in about one hour when the solution became completely clear. The homogeneous solution was cooled to 0° C., and a solution of benzaldehyde (3.8 g) in dimethylsulfoxide (50 ml) was added. The reaction mixture was stirred at room temperature overnight. Most dimethylsulfoxide was removed, and the residue was taken up in ether. The ether solution was washed with water, brine and dried. All solvent was removed and the crude material was chromatographed (silica gel; 5% ethyl acetate in hexanes). Cis-3-cyano stilbene was separated from the minor product which was the trans isomer. Conversion of cis-3-cyano stilbene to the final product, cis-3-hexanoyl stilbene, was carried out in the same manner as described for the trans isomer, trans-3-hexanoyl stilbene in Example 23.

EXAMPLE 23

3-Hexanoyl diphenyl acetylene

Bromine (6.4 g) was added to a solution of trans-3-cyano stilbene (7.2 g) (Example 23) in chloroform (75 ml) and the mixture was refluxed overnight. The solution was washed with a 5% aqueous solution of sodium thiosulfate, water and then dried. On removal of all solvent, the desired stilbene dibromide was obtained as a light brown solid. This crude dibromide was dissolved in dry tetrahydrofuran, and potassium tert-butoxide (7.7 g) was added. The mixture was refluxed overnight. Most solvent was removed and the residue was taken up in ethyl acetate. The organic extract was washed with water, brine and dried. All solvent was removed to obtain the desired acetylenic compound, which was dissolved in ether; a minor impurity which was the corresponding amide, was removed by filtration. 3-Cyanodiphenyl acetylene (3.5 g) was isolated from the ethereal solution.

Conversion of 3-cyanodiphenylacetylene to the final product, 3-hexanoyl diphenyl acetylene, was performed as described under trans-3-hexanoyl stilbene in Example 23.

EXAMPLE 24

3-(2-Phenylethyl)hexanophenone

This compound was prepared by the catalytic reduction ($H_2$, 10% Pd-C, ethanol) of either trans-3-hexanoyl stilbene, cis-3-hexanoyl stilbene or, 3-hexanoyl diphenyl acetylene in nearly quantitative yield.

EXAMPLE 25

Methyl 3-(3-(1-hydroxyethyl)phenoxy)methyl benzoate

A mixture of 3-hydroxyacetophenone (7 g), methyl 3-bromomethyl benzoate (10 g), potassium carbonate (5 g) and potassium iodide (0.2 g) in acetone (75 ml) was refluxed overnight. The reaction mixture was poured into water, and extracted with ethyl acetate. The organic extract was washed with sodium hydroxide solution (1N), water, brine, and then dried. All volatiles were removed, and the residual pale yellow solid (11.5 g) was crystallized from ether. The pure product, methyl 3-(3-acetylphenoxy)methyl benzoate, was isolated as a white solid, m.p. 74.5°–75.5° C.

The above ketone (1.93 g) was dissolved in ethanol (50 ml), and sodium borohydride (0.07 g) was added. The reaction mixture was stirred at room temperature overnight. Excess sodium borohydride was destroyed with cold aqueous hydrochloric acid (1N). The reaction mixture was extracted thoroughly with ethyl acetate. The organic extract was washed with brine, dried over magnesium sulfate and then all solvent was removed. The crude product (1.9 g) was purified by chromatography to yield the desired compound as a colorless liquid.

EXAMPLE 26

3-(3-(1-Hydroxyethyl)phenoxy)methyl benzoic acid

This compound was made by hydrolyzing the corresponding methyl ester, methyl 3-(3-(1-hydroxyethyl)phenoxy)methyl benzoate of Example 29 with sodium hydroxide solution. The desired compound was isolated as white crystals by crystallizing the crude acid from ether-ethanol, m.p. 115°–117° C.

EXAMPLE 27

2-[3-(1-Hydroxyhexyl)phenoxymethyl]-1,2,3,4-tetrahydronaphthalene

A mixture of 4.0 g (0.018 mol) 2-(iodomethyl)-1,2,3,4-tetrahydronaphthalene, 3.4 g (0.018 mol) 3-(1-hydroxyhexyl)phenol and 3.4 ml NaOH (5N) in 50 ml DMSO and 20 ml THF was stirred at room temperature for a period of 48 hours. The reaction mixture was concentrated under reduced pressure. The concentrated reaction mixture was poured into water and extracted with ether. The ether extract was washed with water, dried over $MgSO_4$ and concentrated to dryness under reduced pressure. The residue was passed through a silica gel comumn using hexane/ethyl acetate (3:1) as eluent. Evaporation of eluent gave an oily product (1.3 g).

The product was evaluated for 5-lipoxygenase pathway inhibition (5-LOX/$I_{50}$ $\mu$M) and a value of 6.0 $\mu$M obtained.

EXAMPLE 28

2-(3-(1-Hydroxyhexyl)phenoxymethyl)naphthalene

A suspension of 2-bromomethyl naphthalene (5 g, 0.023 mol), 3-(1-hydroxyhexyl)phenol (5 g, 0.026 mol), powdered potassium carbonate (4.5 g, 0.033 mol), sodium iodide (0.4 g, 0.0023 mol) and cesium carbonate (0.7 g, 0.0021 mol) in dry acetone (75 ml) was refluxed overnight (14 hours). The reaction mixture was filtered, the filtrate was concentrated, dissolved in ether, and then washed successively with 1N NaOH solution 6N HCl solution, water and brine. After drying the organics over anhydrous $MgSO_4$, all volatiles were removed. The crude product (5 g) was further purified by chromatography, using 8% ethylacetate in hexanes on silica gel, to yield 3.5 g of the pure desined compound as a colorless liquid.

The compound was evaluated for 5-lipoxygenase pathway inhibition (5-LOX/$I_{50}$ $\mu$M) and a value of 5.0 $\mu$M obtained.

EXAMPLE 29

2-(3-Hexanoylphenoxy)methyl naphthalene

A mixture containing 2-bromomethyl naphthalene (3.0 g, 13.5 mmol), 3-hexanoylphenol (2.6 g, 13.5 mmol), powdered potassium carbonate (19.0 g, 135 mmol) and potassium iodide (0.1 g) in dry acetone (100 ml) was refluxed for two days. Most of the solvent was removed after filtering off the solid residue. The oil was purified by chromatography on silica gel using a 5% ethylacetate in hexane solution as eluent to leave the desined product as a clear, colorless liquid (2.6 g).

When evaluated, the product showed some 5-lipoxygenase inhibition (5-LOX/$I_{50}$ μM).

The compounds of the present invention have potent activity in regulating the formation of lipoxygenase and as such possess therapeutic value in the treatment of inflammatory conditions and allergic responses such as anaphlaxis and asthma.

Lipoxygenases in mammals have been found in the lung, platelets, and white cells. They are enzymes capable of oxidizing arachidonic acid into hydroperoxyeicosatetraenoic acids (HPETEs) and their stable products hydroxyeicosatetraenoic acids (HETEs). Lipoxygenases are classified according to the position in the arachidonic acid which is oxygenated. Platelets metabolize arachidonic acid to 12-HETE, while polymorphonuclear leukocytes contain 5 and 15 lipoxygenases. It is known that 12-HETE and 5,12-diHETE are chemotactic for human neutrophils and eosinophils, and may augment the inflammation process. 5-HPETE is known to be a precursor of slow-reacting substance of anaphylaxis (SRS-A). The SRS family of molecules, such as leukotrienes B, C, and D, have been shown to be potent bronchoconstrictors (see, NATURE 288, 484–486 (1980)).

The following protocol describes an assay to detect inhibitors of the lipoxygenase pathway. Such inhibitors are believed to be capable of modulating the biosynthesis of the leukotrienes, a property believed to be useful in treating asthma and inflammatory disease states.

Protocol for Detecting Inhibitors of the Lipoxygenase Pathway

A suspension of rat neutrophils in buffer is incubated for 3 minutes at 30° C. with [$^{14}$C]-arachidonic acid (AA) and Calcium Ionophore A23187. Citric Acid (2M) is used to quench the reaction. Following the addition of a trace amount of ($^3$H)-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform and an aliquot is spotted on silica gel TLC sheets, which are developed with an ethyl acetate/isoctane/water/acetic acid solvent system. The 5-HETE spots are visualized with iodine, cut out and placed in scintillation vials for counting. After adjusting for the extraction efficiency, the amount (pmole) of [$^{14}$C]-5-HETE in each of the tubes is quantitated. The net pmoles of 5-HETE are obtained by substracting the pmoles of 5-HETE in the tubes containing buffer alone (blank) from the pmoles of 5-HETE in the tubes containing buffer and cells (control). The ability of the test compounds to modulate the activity of this enzyme is determined by a decrease or increase in the net amount of 5-HETE produced.

In Table I the last column shows the concentration required for 50% inhibition of the 5-lipoxygenase pathway (5-LOX/$I_{50}$ μM) for representative compounds according to the present invention (i.e. the aryleicosanoids described herein).

TABLE I $Ar_1-X-Ar-Z-(R)_{n'}$

| $Ar_1$ | X | Ar | $Z(R)_{n'}$ | 5-LOX $I_{50}$ μM |
|---|---|---|---|---|
| 3-carboxyphenyl | CH$_2$O | C$_6$H$_4$* | 3-(CHC$_5$H$_{11}$)**<br>\|<br>OH | 25 |
| 2-carboxyphenyl | CH$_2$O | C$_6$H$_4$ | 3-(CHC$_5$H$_{11}$)<br>\|<br>OH | 30 |
| 2-carboxyphenyl | CH$_2$O | C$_6$H$_4$ | 3-(CHC$_4$H$_9$)<br>\|<br>OH | 10 |
| 4-carboxyphenyl | CH$_2$O | C$_6$H$_4$ | 3-(CHC$_5$H$_{11}$)<br>\|<br>OH | 21 |
| 3-carbomethoxyphenyl | CH$_2$O | C$_6$H$_4$ | 3-(CHC$_5$H$_{11}$)<br>\|<br>OH | 1.2 |
| 2-carbomethoxyphenyl | CH$_2$O | C$_6$H$_4$ | 3-(CHC$_5$H$_{11}$)<br>\|<br>OH | 0.6 |
| 2-carbomethoxyphenyl | CH$_2$O | C$_6$H$_4$ | 3-(CHC$_4$H$_9$)**<br>\|<br>OH | 3.0 |
| 4-carbomethoxyphenyl | CH$_2$O | C$_6$H$_4$ | 3-(CHC$_5$H$_{11}$)<br>\|<br>OH | 3.2 |
| 3-carbomethoxyphenyl | CH$_2$O | C$_6$H$_4$ | 2-(CHC$_5$H$_{11}$)<br>\|<br>OH | 3.2 |

TABLE I-continued

Ar₁—X—Ar—Z—(R)ₙ'

| Ar₁ | X | Ar | Z(R)ₙ' | 5-LOX I₅₀ μM |
|---|---|---|---|---|
| 3-carboxymethylphenyl | CH₂O | C₆H₄ | 3-(CHC₅H₁₁)<br>\|<br>OH | |
| 3-carbomethoxymethylphenyl | CH₂O | C₆H₄ | 3-(CHC₅H₁₁)<br>\|<br>OH | 5.8 |
| 3-carbomethoxyphenyl | CH₂O | C₆H₄ | 3-(CHC₅H₁₁)<br>\|<br>OCOCH₃ | 5.0 |
| 3-carbomethoxyphenyl | CH₂O | C₆H₄ | 3-(CHC₅H₁₁)<br>\|<br>OCH₃ | 10 |
| 3-carbomethoxyphenyl | CH₂O | C₆H₄ | 3-(CHC₅H₁₁)<br>\|<br>OTHP*** | 23 |
| 2-carbomethoxyphenyl | CH₂O | C₆H₄ | 3-(CHC₄H₉)<br>\|<br>OTHP | 10 |
| 2-hydroxymethylphenyl | CH₂O | C₆H₄ | 3-(CHC₄H₉)<br>\|<br>OH | 4 |
| 3-formylphenyl | CH₂O | C₆H₄ | 3-(CHC₄H₉)<br>\|<br>OH | 4.0 |
| 3-cyanophenyl | CH₂O | C₆H₄ | 3-(CHC₅H₁₁)<br>\|<br>OH | 17 |
| 3-aminomethylphenyl | CH₂O | C₆H₄ | 3-(CHC₅H₁₁)<br>\|<br>OH | |
| 3-carbamylphenyl | CH₂O | C₆H₄ | 3-(CHC₅H₁₁)<br>\|<br>OH | 2.0 |
| 4-acetoxymethoxyphenyl | CH₂O | C₆H₄ | 3-(CHC₅H₁₁) | 4.8 |
| phenyl | CH₂O | C₆H₄ | 3-(CHC₅H₁₁)<br>\|<br>OH | 2.7 |
| phenyl | OCH₂ | C₆H₄ | 3-(CHC₅H₁₁)<br>\|<br>OH | 6.7 |
| 3-carbomethoxyphenyl | CH₂O | C₆H₄ | 3-(C=CHC₄H₉)<br>\|<br>CH₃ | 5.0 |
| 3-carbomethoxyphenyl | CH₂O | C₆H₄ | 4-(CH=CHC₄H₉) | 100 |
| phenyl | CH₂O | C₆H₄ | 3-(C—C₅H₁₁)<br>\|\|<br>O | 2.0 |
| phenyl | CH₂O | C₆H₄ | 3-[CC(CH₃)₂C₄H₉]<br>\|\|<br>O | 7.5 |
| phenyl | CH₂O | C₆H₄ | 3-[CHC(CH₃)₂C₄H₉]<br>\|<br>OH | 2.5 |
| phenyl | CH₂O | C₆H₄ | 3-[CHCH(CH₃)C₄H₉]<br>\|<br>OH | 3.0 |
| 3-carbomethoxyphenyl | CH₂O | C₆H₄ | 3-[CHC(CH₃)₂C₄H₉]<br>\|<br>OH | 2.0 |

TABLE I-continued $Ar_1-X-Ar-Z-(R)_{n'}$

| $Ar_1$ | X | Ar | $Z(R)_{n'}$ | 5-LOX $I_{50}$ μM |
|---|---|---|---|---|
| phenyl | $CH_2O$ | $C_6H_4$ | 3-[C(CH_3)C_5H_{11}]<br>             OH | 1.0 |
| phenyl | $CH_2O$ | $C_6H_4$ | 3-[C(CH_3)C(CH_3)_2C_4H_9]<br>             OH | 2.4 |
| phenyl | $CH_2O$ | $C_6H_4$ | 3-(CHC_5H_{11})<br>      NHCH_3 | 22 |
| phenyl | trans CH=CH | $C_6H_4$ | 3-(CHC_5H_{11})<br>      OH | 4.5 |
| 3-carbamylphenyl | $CH_2O$ | $C_6H_4$ | 3-(CC_5H_{11})<br>      ‖<br>      O | 0.7 |
| 3-cyanophenyl | $CH_2O$ | $C_6H_4$ | 3-(CC_5H_{11})<br>      ‖<br>      O | 8.0 |
| phenyl | —O— | $C_6H_4$ | 3-(CHC_5H_{11})<br>      OH | 1.2 |
| 3-trifluoromethylphenyl | $CH_2O$ | $C_6H_4$ | 3-(CHC_5H_{11})<br>      OH | 3.0 |

*$C_6H_4$ is phenylene
**$C_5H_{11}$ and $C_4H_9$ are linear alkyl
***THP is tetrahydro-2H—pyran-2yl- Leukotrienes, the products of the 5-lipoxygenase pathway of arachidonic acid metabolism, are potent contractile agents with a variety of smooth muscle preparations. Thus, it has been hypothesized that the leukotrienes contribute significantly to the pathophysiology of asthma. The following protocol describes an in vitro assay used to test compounds which specifically antagonize the actions of leukotrienes.

Protocol for SRS-A (slow reacting substance of anaphylaxis) Antagonists

Peripheral strips of guinea pig lungs are prepared and hung in tissue baths (Metro #ME-5505, 10 ml) according to the published procedure (Proc. Nat'l Acad. Sci, U.S.A. Volume 77, pp. 4354–4358, 1980). The strips are thoroughly rinsed in Assay Buffer and then connected with surgical silk thread to the support rods from the tissue baths. The rods are adjusted in the baths and the strips connected to the pressure transducers (Grass FT 103 or Gould UC-3). The tissue baths are aerated with 95% oxygen-5% carbon dioxide and maintained at 37° C. The Assay Buffer has been made as follows: For each liter of buffer the following are added to approximately 800 ml of water distilled in glass—6.87 g. NaCl, 0.4 g. KCl, 2.1 g. $NaHCO_3$, 0.14 g. $NaH_2PO_4.H_2O$, 0.21 g. $MgSO_4.7H_2O$, and 2.0 g. D-glucose. Then a solution of 0.368 g. $CaCl_2.2H_2O$ in 100 ml glass-distilled water is slowly added to the buffer. Sufficient water is added to adjust the volume to one liter, and the solution is aerated with 95% oxygen-5% carbon dioxide. Usually 10 liters of buffer are used for an experiment with 4 tissues.

After the tissues have been repeatedly washed and allowed to equilibrate in the tissue bath, they are challenged with 1 μM histamine. After maximum contractions have been obtained, the tissues are washed, and allowed to relax back to baseline tension. This histamine challenge procedure is repeated at least 1 to 2 more times to obtain a repeatable control response. The average response to 1 μM histamine for each tissue is used to normalize all other challenges.

Responses of each tissue to a pre-determined concentration of leukotriene are then obtained. Usually test compounds are examined initially at 30 μM on resting tension of the tissues without any added agonist or antagonist to determine if the compound has any possible intrinsic activity. The tissues are washed, and the test compound is added again. Leukotriene is added after the desired pre-incubation time. The intrinsic activity of the compounds, and their effect on leukotriene-induced contractions are then recorded.

The concentration required for 50% inhibition of 0.2 nM leukotriene $C_4$-induced contraction of guinea pig peripheral strips for representative compounds of the present invention is shown in Table II.

TABLE II

ARYLEIOCOSANOIDS AS SRS-A Antagonists

| No.* | SRS-A Antagonist $I_{50}$ μM |
|---|---|
| 2 | 20 |
| 3 | 20 |
| 10 | 40 |
| 37 | 30 |

*Numbers correspond to numbers and compounds identified by their chemical structures in Table I.

Representative compounds of the present invention were also tested in the following in vivo model.

Protocol for in vivo Testing of Modulators of SRS-A (slow reacting substances of anaphylaxis)

This test, known as the Bronchial Anaphylaxis in Guinea Pigs with Enhanced Leukotrines (BAGEL), is based on the procedure published in Agents and Actions, Vol. 11, pp. 396–401, 1981, and is performed with guinea pigs actively immunized (14 days) with ovalbumin (2.7 mg/kg, i.p.) and B. pertussis ($5 \times 10^9$ organisms) as an adjuvant. Prior to challenge with antigen (ovalbumin), the animals are anesthetized and prepared for monitoring pulmonary dynamics by whole body plethysmography. They are treated with an $H_1$ antihistamine (methapyrilene, 2 mg/kg, i.v.) and cyclooxygenase inhibitor (indomethacin; 20 mg/kg, i.p.) in order to enhance the SRS-A component of anaphylactic bronchoconstriction. Bronchoconstriction is quantified as the maximum increase in airway resistance following antigen challenge. The drug is administered either i.p. 10 minutes before challenge, or i.d. 15 minutes before challenge.

In Table III are shown results of testing a few compounds of the present invention according to this protocol.

TABLE III

| ARYLEICOSANOIDS AS SRS-A MODULATORS | |
|---|---|
| No.* | BAGEL |
| 20 | H at 200 mg/Kg, i.d. |
| 24 | M at 100 mg/Kg, i.v. |
| 37 | H at 200 mg/Kg, i.p. |

*Numbers correspond to numbers and compounds identified by their chemical structures in Table I.
Rating System (mean of ≧2 trials):
H: <150% increase in airway resistance
M: 150–300% increase in airway resistance By following the procedure of the foregoing examples, the following compounds are also prepared:
2-[2-(1-hydroxy hexyl)-5-pyridyloxy]benzene;
2-[2-(2-hydroxy hexyl)-3-pyranyloxy]benzene;
2-[2-(2-hydroxy heptyl)-4-thiopyranyloxy]benzene;
2-[2-(2-hydroxy heptyl)-5-quinolyloxy]benzene;
2-(3-(1-hydroxy-6,6,6-trifluorohexyl)phenoxymethyl)-1,4-naphthaquinone;
1-(3-(1-hydroxy-1-methylhexyl)-phenoxymethyl)-2-methoxy naphthalene;
1-(3-(6-phenoxy-1-hydroxyhexyl)phenoxymethyl)-4-methoxy naphthalene;
2-(1-(3-(1-hydroxy-2,2-dimethylhexyl)phenoxy)ethyl)naphthalene;
9-(3-(1-hydroxyhexyl)phenoxymethyl)anthracene;
9-(3-(1-hydroxyhexyl)phenoxymethyl)phenanthrene.

What is claimed is:
1. 2-(3-(1-Hydroxyhexyl)phenoxymethyl)naphthalene.
2. 2-(3-(1-Hydroxyhexyl)phenoxymethyl)-1,2,3,4-tetrahydronaphthalene.
3. 1(3-(1-hydroxy-1-methylhexyl)phenoxymethyl)-2-methoxy naphthalene.
4. 1-(3-(6-phenoxy-1-hydroxyhexyl)phenoxymethyl)-4-methoxy naphthalene.
5. 2-(1-(3-(1-hydroxy-2,2-dimethylhexyl)phenoxy)ethyl naphthalene.

* * * * *